United States Patent [19]

Reiner

[11] Patent Number: 5,009,487
[45] Date of Patent: Apr. 23, 1991

[54] PRISM SYSTEM FOR A STEREOSCOPIC MICROSCOPE

[75] Inventor: Josef Reiner, Cologne, Fed. Rep. of Germany

[73] Assignee: Oculus Optikgeraete GmbH, Wetzlar, Fed. Rep. of Germany

[21] Appl. No.: 386,735

[22] Filed: Jul. 28, 1989

[30] Foreign Application Priority Data

Jul. 30, 1988 [DE] Fed. Rep. of Germany ....... 3826069

[51] Int. Cl.$^5$ .......................... G02B 5/04; G02B 21/22
[52] U.S. Cl. .................................. 350/286; 350/507; 350/515
[58] Field of Search ................ 350/506–522, 350/523, 542, 544, 170–174, 320, 321, 286, 287, 130–145

[56] References Cited

U.S. PATENT DOCUMENTS

| | | | |
|---|---|---|---|
| 1,679,661 | 8/1928 | Hugershoff | 350/138 |
| 2,057,921 | 10/1936 | Santoni | 350/517 |
| 4,174,884 | 11/1979 | Weissler | 350/138 |
| 4,518,231 | 5/1985 | Muchel et al. | 350/516 |
| 4,594,608 | 6/1986 | Hatae et al. | 350/515 |
| 4,601,550 | 7/1986 | Yoshio et al. | 350/516 |
| 4,614,411 | 9/1986 | Hörenz | 350/516 |
| 4,643,541 | 2/1987 | Matsubara | 350/516 |
| 4,704,012 | 11/1987 | Kohayakawa et al. | 350/516 |
| 4,710,000 | 12/1987 | Spitznas et al. | 350/516 |
| 4,723,842 | 2/1988 | Twisselmann et al. | 350/511 |
| 4,786,154 | 11/1988 | Fantone et al. | 350/515 |

FOREIGN PATENT DOCUMENTS

| | | |
|---|---|---|
| 2483581 | 3/1983 | Fed. Rep. of Germany . |
| 214223 | 10/1984 | Fed. Rep. of Germany ...... 350/515 |
| 240614 | 11/1986 | Fed. Rep. of Germany ...... 350/515 |
| 3622126 | 3/1987 | Fed. Rep. of Germany . |

OTHER PUBLICATIONS

Book, "Bauelemente der Optik", H. Naumann/G. Schroeder, 2 title pages, and pp. 176 and 177.

Primary Examiner—Paul M. Dzierzynski
Assistant Examiner—Thong Nguyen
Attorney, Agent, or Firm—Flynn, Thiel, Boutell & Tanis

[57] ABSTRACT

A prism system for a stereoscopic microscope in which both an image inversion and also an interchanging of the sides of the two beam paths can occur. In order to achieve a reliable simply constructed design of a small size, the prism system has four reflecting surfaces for each beam path, of which two surfaces are constructed as reflection surfaces and are arranged in planes parallel with respect to the optic longitudinal axis. The two other surfaces are constructed as inlet or rather outlet surfaces and are inclined at 45° with respect to the optic longitudinal axis and at 90° with respect to one another. The inventive prism system makes it possible with a distinctly low structural height to interchange beam paths which are parallel with one another, and to carry out an image inversion at the same time. The prism system according to the invention can be utilized in particular in stereoscopic microscopes to carry out surgeries, in particular eye surgeries.

13 Claims, 3 Drawing Sheets

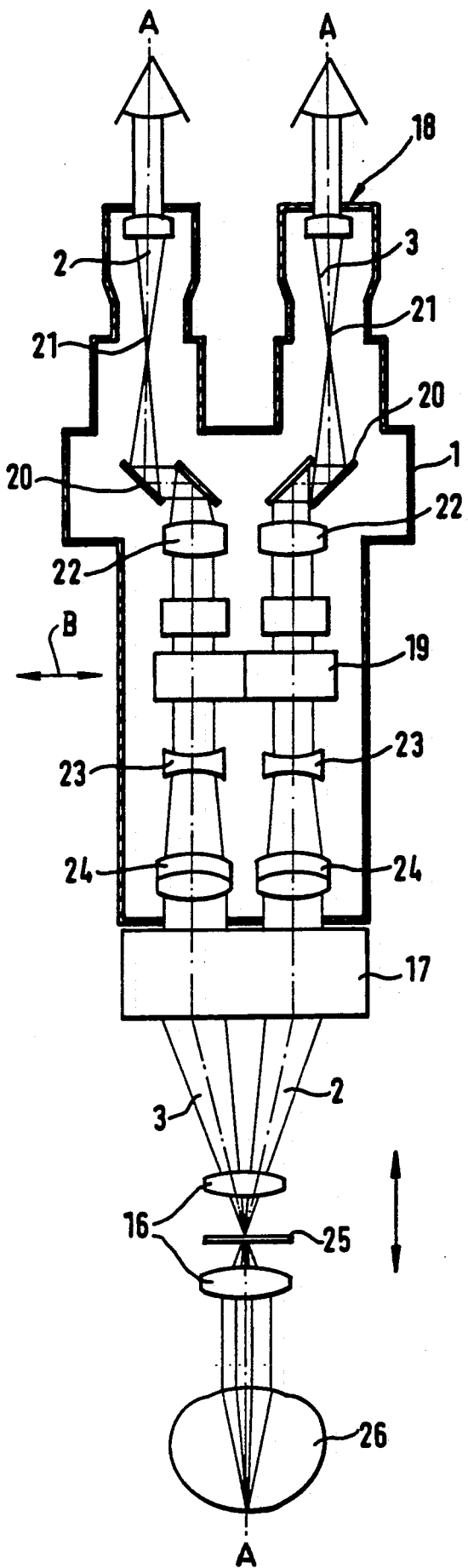
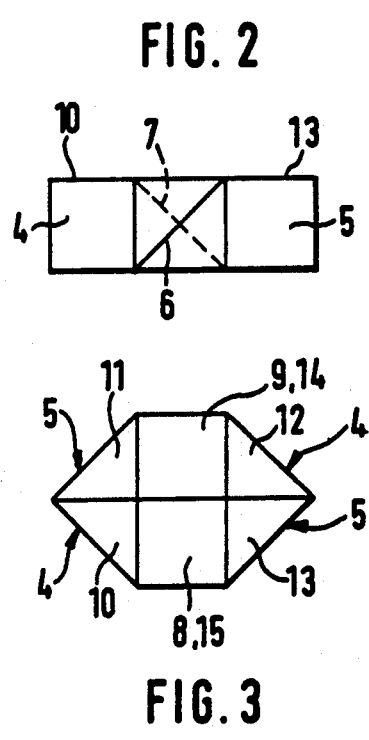
FIG. 4
FIG. 2
FIG. 3

PRISM SYSTEM FOR A STEREOSCOPIC MICROSCOPE

FIELD OF THE INVENTION

The invention relates to a prism system for a stereoscopic microscope comprising several reflecting surfaces deflecting a right and a left beam path each at 90° and, more particularly, a stereoscopic microscope for use during surgeries comprising a lens device and two ocular arrangements.

BACKGROUND OF THE INVENTION

In surgeries using a stereoscopic microscope, for example in the field of ophthalmology, neurosurgery, otology, etc., usually microscopes with a weak magnification are used. They have separate beam paths in order to make possible a stereoscopic viewing of the surgery field by the surgeon. Ocular systems are thereby utilized, each of which include an ocular tube. Furthermore, one common lens is usually used for both beam paths, in which a common collective lens is provided in most cases.

Diverging beams enter the lens in such a microscope, which beams are guided parallel through the lens systems and are directed to the magnification changer. The beams exit from the changer again in the form of parallel beams and are fed to the respective ocular system or ocular tube.

In the case of common stereoscopic microscopes suited for surgical purposes, it may be necessary to provide additional optic elements between the lens and the magnification changer or between the magnification changer and the ocular system, for example, beam splitters for optic recording devices or for co-observer systems. The use of this additional element results in a considerable increase of the structural length of the microscope, which is undesired both for technical use reasons and also for optic reasons. The structural length of the microscope is limited in technical use respects since the surgeon must carry out the surgery and at the same time also must watch same through the microscope. With respect to optic reasons, it is always desirable to keep the size of an optic device as small as possible, since an increase of the structural length results in a limitation of the optic field of vision and in addition is negatived by the loss of light.

The limitation of the field of vision is particularly disadvantageous for surgeries on the vitreous body of an eye or rather in the vitreous body area, since it is not possible or only possible under considerable difficulties to overlook the entire area subject to surgery. It is therefore desirable to expand the field of vision angle as much as possible, for example up to a value of 150°.

A further problem occurring in such stereoscopic microscopes results when the microscope is supposed to be used with an in-between image. An in-between image becomes necessary when, for example, the retina or the vitreous body area of the eye of the patient is supposed to be viewed. A collecting system in the form of a contact glass or a lens is in such a case usually applied onto or in front of the patient's eye. The optic system of the eye and the contact glass or the supplementary lens produce thereby a true image of the retina or of a plane of the vitreous body area. The true image is behind the contact glass or rather the supplementary lens and is used when the microscope is adjusted for focusing. Due to the optic relationships, this true image appears inverted and interchanged with respect to the sides. The interchanging of sides results in an inverse stereoscopic effect, which in turn causes the surgeon to recognize the foreground or the background of the stereoscopic image interchanged.

In order to overcome this interchanging of the stereoscopic effect and in order to reproduce the image in a correct manner, it is necessary, aside from the image inversion, to also carry out a change of the beam paths, namely, an interchanging of the right and the left beam path in the area of the microscope European A1-193 818 (which corresponds to U.S. Pat. No. 4,710,000) describes a stereomicroscope, in which the stereoscopic inversion and the image inversion is overcome by means of a prism arrangement or a prism system. However, this known prism system proves to be disadvantageous in some cases because of its size, with the size not only influencing the outside dimensions of the microscope, but also the length of the optic path. By extending the optic path, limitations of the field of vision and undesired light losses result in turn.

German OS 36 15 842 (which corresponds to U.S. Pat. No. 4,723,842) also discloses a prismatic intermediate assembly which is relatively large and consequently has the disadvantages known from the above-mentioned EP-A1-193 818.

The Book Naumann-Schroeder "Bauelemente der Optik", Hanser Verlag, discloses various prism systems for image inversion and for lateral shifting, which in general show the possibility for use of prisms.

The basic purpose of the invention is to provide a prism system or rather a stereoscopic microscope of the above-mentioned type, which with a simple design, a small size and high performance can avoid the disadvantages of the state of the art and can be manufactured inexpensively.

The invention provides a prism system, for a stereoscopic microscope having a plurality of deflecting surfaces each deflecting a right or left beam path by 90°, wherein four reflecting surfaces are provided in each beam path, wherein two of the surfaces in each beam path are each a reflection surface arranged in a plane parallel with respect to the optic longitudinal axis of the microscope, and wherein the two other surfaces are respectively inlet and outlet surfaces and are inclined at 45° with respect to the optic longitudinal axis and at 90° with respect to one another.

The inventive prism system is distinguished by a number of considerable advantages. By using four reflecting surfaces in each beam path, it is possible to guide the individual beams of the right or left beam path independently from one another in an exact manner so that on the one hand the inverted stereoscopic effect is removed and on the other hand an image inversion is carried out. With the separation into reflection surfaces and inlet or outlet surfaces, it is possible to arrange the individual surfaces separately from one another so that as a whole a design is created which, with the smallest structural dimensions, assures the highest degree of optic efficiency. Since the inlet or outlet surfaces are each inclined at 45° with respect to the optic longitudinal axis and define an angle of 90° with respect to one another, it is possible, while maintaining the same optic direction of the entering and exiting light beams of the prism system, for a narrow spacial association of the inlet and outlet surfaces to occur.

A particularly advantageous development of the invention provides that the surfaces arranged in planes parallel with respect to the optic longitudinal axis each define an angle of 90° with respect to one another. Thus, it is possible to design the entire prism system with respect to its outside dimensions substantially square or rectangularly, with the base of the square or rectangle being able to be adjusted in a simple manner to the structural demands of the microscope. Since the right and the left beam path is guided parallel to the base of the rectangle or square, a definitely low structural height can be achieved, which proves to be particularly advantageous with respect to the entire construction of the microscope, since the entire length of the microscope must only be increased insignificantly in order to store the inventive prism system.

The reflecting surfaces are in a further advantageous development of the invention each constructed as hypotenuse surfaces of a rectangular prism member. This development has the advantage that the reflection of the light beam occurs inside of the prism member and that the light beams are not again broken when entering or exiting the prism member. A further advantage of this development lies in both the manufacture and also the assembly operations of the prism system being able to be significantly simplified.

Furthermore, it can be advantageous when the prism member includes an inlet surface of the one beam path on the prism member having the outlet surface of the other beam path, with both surfaces adjoining one another. Two prism members are in this development united to form a cube or cubical-shaped element, so that a particularly good utilization of the available spacial relationships is possible. A further advantage lies in the inlet or outlet surface being protected against damage, since these are covered by the respectively adjacent prism member.

Furthermore, it can be advantageous to arrange the prism members having the reflection surfaces each resting against one another or designing these so that they rest on the adjoining prism members including the inlet surface or the outlet surface. Since these prism members, which have the reflection surfaces, are arranged such that the reflection surfaces are on the outer periphery of the prism system, it is possible to significantly minimize the dimensions of the entire arrangement. It can thereby be furthermore advantageous to construct two of the prism members in one piece in each beam path. Loss of light during the entry or exit into the prism member medium is avoided by this measure. Furthermore, it is also possible to construct these prism members in one piece with the adjoining prism members having the inlet or outlet surface, so that the entire prism arrangement of the inventive prism system can be built of only two individual members. Such a development is particularly advantageous also in view of possible disadjustments, since individual adjustment of the individual reflection surfaces during installation into the microscope is no longer needed.

The reflecting surfaces can be either of the minor type with a reflecting coating, or, by selecting suitable materials of a total reflection type. Those of ordinary skill in the optic art are thoroughly familiar with conventional reflecting coatings and with conventional principles of material selection to effect total reflection, and thus those principles are not, in and of themselves, disclosed herein in detail. The specific materials selected to effect total reflection would depend on the wavelengths to be used, the structural dimensions, and the required optic qualities.

The purpose is attained with respect to the stereoscopic microscope by providing a prism system in an area of the microscope which includes two parallel beam paths. This development of the microscope has the advantage that no additional measures are needed for deflecting the beam path, since the already provided parallel beam paths can be used directly for transmission through the prism system.

The inventive prism system can be arranged in the inventive microscope between a collective lens, which is provided in the area of the lens device, and a magnification changer, which is provided in beam direction after the lens. However, it is also possible to provide the prism system between the ocular arrangement and the magnification changer. Thus, it is inventively particularly advantageous that the prism system can be inserted at any desired area of the microscope anywhere where parallel beam paths exist. Thus, it is possible to use the inventive prism system in connection with conventional microscope developments without requiring conversions or changes to the microscope.

A particularly advantageous further development of the inventive microscope is that the prism system, while maintaining the normal function of the microscope, can be removed from the beam path of same. The prism system can be moved or tilted, such that its movement is effected in the X- or Y-direction with respect to the optic axis of the microscope. This microscope development permits a quick change between a normal viewing through the stereoscopic microscope and a viewing of the surgery field using the inventive inverting prism system. Since no conversions of the microscope are needed in the inventive microscope for removing the prism system, the change can also be carried out quickly and easily by an unschooled operator. Furthermore, it has proven to be advantageous that the inventive prism system is very small, so that both the space needed for the change of the viewing manner can be dimensioned very small and also the required forces can be minimized. The latter is particularly important when the microscope, during surgery, must be held vibration-free on the eye of a patient. A further advantage is that in the inventive microscope upon removal of the inventive prism system, the normal viewing manner remains uninfluenced by the microscope, since the parallel beam paths can, upon removal of the prism system, continue to be guided parallel unhindered.

BRIEF DESCRIPTION OF THE DRAWINGS

The invention will be described hereinafter in connection with one exemplary embodiment and the drawings, in which:

FIG. 2 is a side view of the prism system of FIG. 1 assembled ready for use;

FIG. 3 is a top view of the prism system illustrated in FIG. 2;

FIG. 4 is a schematic illustration of the inventive microscope;

DETAILED DESCRIPTION

Figure 1:
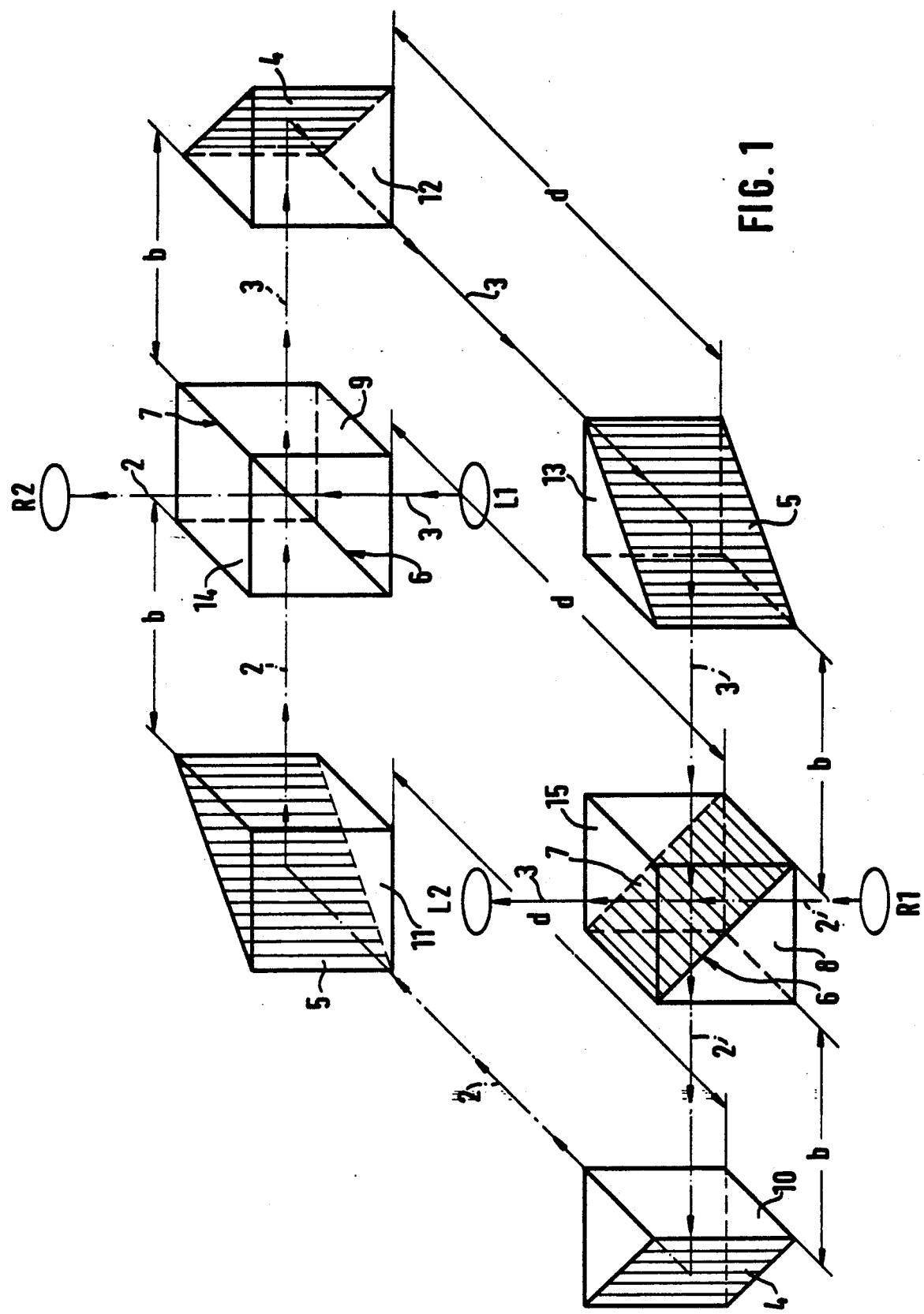
FIG. 1 is a schematic, isometric illustration of the inventive prism system.

FIG. 1 schematically illustrates the inventive prism system, with the individual elements of the prism system being shown separately from one another in order to make understanding of the invention easier.

Two parallel beam paths $R_1$ and $L_1$ are shown in FIG. 1 and, in a manner which will yet have to be described, are constructed in a stereoscopic microscope. The beam paths are, in the prism system shown in FIG. 1, diverted several times independently from one another and are again sent out in a parallel arrangement as beam paths $R_2$ and $L_2$. The inventive prism system is constructed such that both an interchanging of the sides of the beam paths, namely, a change from the right to the left beam path and vice versa occurs, and also an image inversion.

The inventive prism system has two reflection surfaces 4, 5 for the right and the left beam path, which reflection surfaces are aligned parallel to an optic longitudinal axis A (see FIG. 4), with the optic longitudinal axis A being parallel to the beam paths 2, 3. The entering beam paths 2, 3 are fed to the reflection surfaces 4, 5 through inlet surfaces 6. The deflection of the exiting light beams of the beam paths 2, 3 is done by the also reflecting outlet surfaces 7. As shown in FIG. 1, the inlet surfaces 6 or rather the outlet surfaces 7 are each arranged at an angle of 90° to one another and form an angle of 45° with respect to the optic longitudinal axis A or rather with respect to the inlet and outlet direction of the beam paths 2, 3.

The operation of the inventive prism system will be described hereinafter in connection with the schematic illustration of FIG. 1. Since the inventive prism system is symmetrically designed with respect to the right and left beam path, only the right beam path ($R_1$) will first be described. For simplicity reasons, only one beam is illustrated which has the reference numeral 2. The beam path 2 encounters the inlet surface 6 parallel with respect to the optic longitudinal axis A of the microscope 1 and is deflected at 90° by the inlet surface, since the inlet surface 6 is arranged at an angle of 45° with respect to optic longitudinal axis A. In the illustration according to FIG. 1, the beam path 2 is deflected to the left. The beam path 2 subsequently encounters the reflection surface 4 which effects another deflection at 90°, so that the light beam or beam path 2 is guided to the reflection surface 5, which also effects a deflection at 90°. The beam path 2 then encounters the outlet surface 7 which is also inclined at 45° with respect to the direction of the optic longitudinal axis A and deflects the beam path 2 again at 90°. The exiting beam path 2 ($R_2$) is thus parallel to the entering beam path 2 ($R_1$), however, was laterally offset and subjected to an image inversion.

The left beam path ($L_1$) identified by the reference numeral 3 encounters, parallel aligned with respect to the optic longitudinal axis A or rather to the beam path 2 ($R_1$), the other inlet surface 6, is deflected at 90° by the inlet surface, encounters the reflection surface 4, is again deflected at 90° and guided to the reflection surface 5, which directs the beam path 3 again to the outlet surface 7 which effects a further 90° deflection. The deflection of the left beam path 3 occurs, so far, symmetrically with respect to the deflection of the right beam path 2.

FIG. 1 illustrates that the entering right beam path $R_1$ is aligned with the exiting left beam path $L_2$, while the entering left beam path $L_1$ is arranged coaxially with respect to the exiting right beam path $R_2$. Thus, a reversal of sides or an interchanging of sides of the right and left beam paths occurs by means of the inventive prism system.

The inventive prism system includes several prism members 8 to 15, each of which is a rectangular prism member having a hypotenuse surface functioning as a reflection surface. According to the above-described arrangement and operation, the respective beam paths 2, 3 first encounter the inlet prism members 8 and 9 and are guided by the prism members through the following prism members 10, 11 or 12, 13 prior to reaching the outlet prism members 14 or 15. The inlet prism members 8, 9 and the outlet prism members 14, 15 are each arranged in pairs with one another such that an outlet surface 7 is associated with the respective inlet surface 6. The prism members 9, 14 and 8, 15 respectively thus each form a cube or quadrangular prism, with the reflection surfaces 6 and 7 being inner surfaces of the quadrangular prism. According to the invention, the respective prism members 8, 15 and 9, 14 can be secured relative one another, for example by adhesives, cementing or the like. Since the prism members 10 to 13 are constructed and arranged such that their reflecting hypotenuse surfaces point outwardly, it is possible to adjust the distance d and b between the prism members 8 to 15 to meet requirements of a particular application. The distances b and d are reduced to zero in the exemplary embodiment illustrated in FIGS. 2 and 3, so that the inventive prism system is embodied by a single member having a minimum overall volume. The dimensions of the distances d and b depend on the respective structural requirements, with the distances between the right and left beam paths having to be considered in a suitable manner.

Thus, with the aid of the inventive prism system both an image inversion and also a beam inversion or lateral interchanging of the right with the left beam path takes place. The parallelism of the beam paths or rather their coaxial arrangement is thereby maintained unchanged.

FIG. 2 illustrates a side view of the inventive prism system according to FIG. 1 assembled ready for use, with the distances b and d, as already mentioned, being reduced to zero. FIG. 3 is a top view of the prism system shown in FIG. 2. FIGS. 2 and 3 do not show the beam paths 2 and 3 in order to have a clearer illustration.

FIG. 4 schematically illustrates an inventive stereoscopic microscope which is provided with the inventive prism system. The microscope 1 includes, in the usual manner, a housing shown only schematically, on which an ocular arrangement 18 is arranged, which in the usual manner can be constructed in the form of a telescope ocular tube. A diaphragm 21 can be provided following the ocular arrangement, through which diaphragm the beam paths 2, 3 are guided to a deflecting prism arrangement 20. The prism arrangement 20 can be constructed in the usual manner. Lenses 22 are provided following the prism arrangement 20, which lenses effect a parallel alignment of the beam paths 2 and 3. The inventive prism arrangement 19 is arranged in the parallel beam path, which prism arrangement is only schematically illustrated in FIG. 4 and has the design illustrated in FIGS. 1 to 3. Lenses 23 and 24 are each provided following the prism arrangement or the prism system 19, which lenses 23 and 24 can divert or again parallel align the beam paths 2, 3. A magnification changer 17 is provided following the lens 24, which changer 17 can be designed in the usual manner and makes possible a change of the magnification relationships. Thus, a detailed description of the magnification changer 17 is not needed. The magnification changer 17 is followed by collective lenses 16, by means of which the beam paths starting out from an image plane 25 can be focussed. An eye 26 of a patient is shown below the image plane 25. The eye 26 is thereby only schematically illustrated.

Thus, in the inventive microscope the light exiting in the area of the eye 26 of the patient or rather the image produced in the image plane 25 is guided through the collective lenses 16, the magnification changer 17, the lenses 24 and 23 to the inventive prism system 19, is inverted and laterally interchanged therein and is guided through the lenses 22 to the deflecting prism arrangement 20 effecting a lateral shifting of the beam paths 2, 3 in order to permit an adjustment to the interocular distance of the observer. The beam paths 2, 3 are thereafter guided through the diaphragm 21 to the ocular arrangement 18.

The inventive prism system 19 has a very small thickness, for example 18 mm, and thus facilitates a use with a common microscope without special changes or structural reconstructions.

As illustrated by the arrow B in FIG. 4, it is possible without interfering with the operation of the microscope to remove the prism arrangement 19 or rather the inventive prism system out of the beam path by a lateral shifting or pivoting thereof in order to be able to use the microscope in the usual manner.

Figure 5:
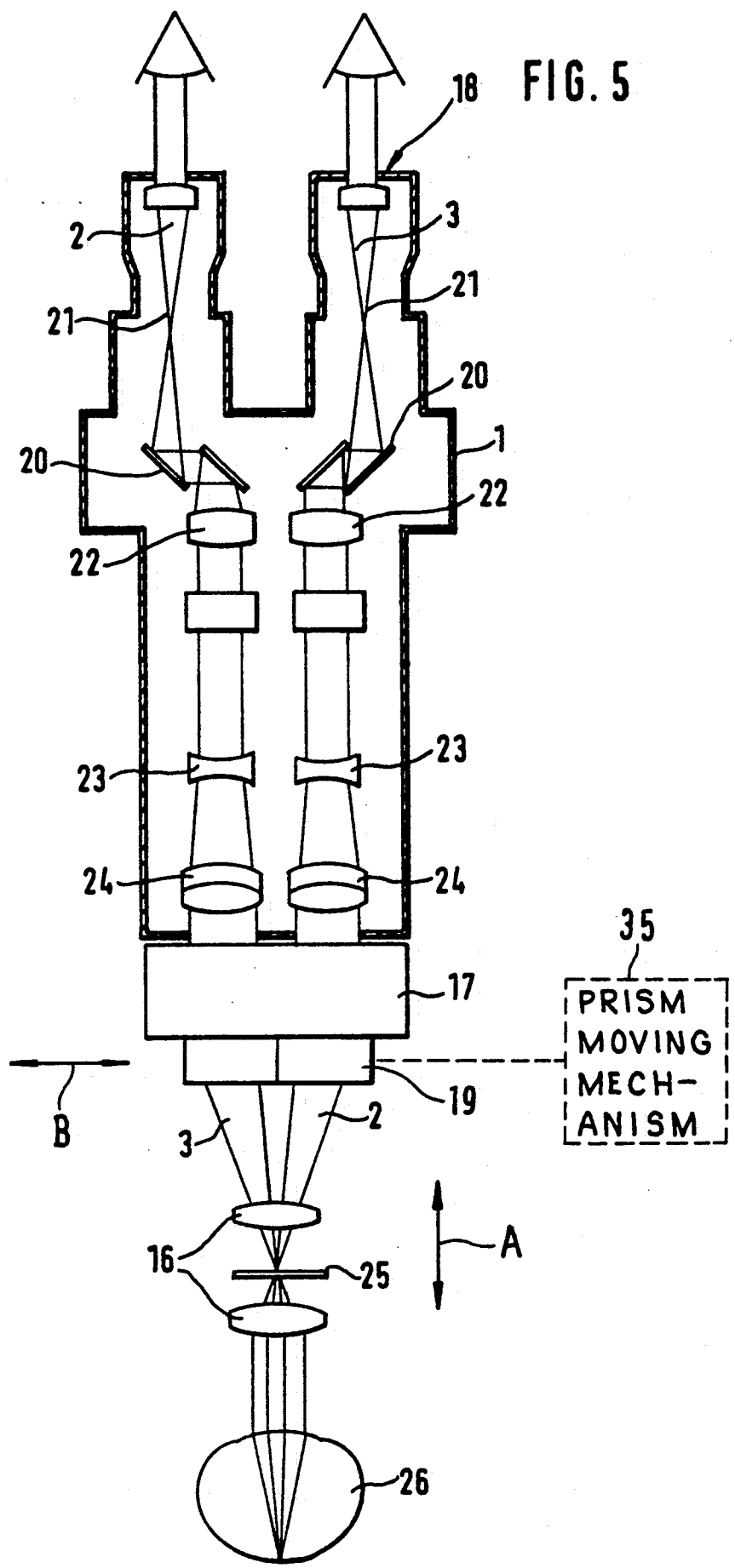
FIG. 5 is a schematic illustration similar to FIG. 4 of a different embodiment.

FIG. 5 illustrates an alternate embodiment, which is substantially identical to the embodiment of FIG. 4 except for the following differences. First, the prism arrangement 19 has been relocated so that it is disposed between the collective lenses 16 and the magnification changer 17. Second, a prism moving mechanism 35 is depicted, and moves the prism arrangement 19 in the direction of arrows B between the illustrated position in which it is disposed in the beam path of the microscope and a further position in which it is not disposed in the beam path. The mechanism 35 is conventional, and is not in and of itself the subject of the present invention.

The invention is not to be limited to the illustrated exemplary embodiment, rather many possibilities for modifications exist in particular with respect to the dimensioning of the prism system and the association of the reflection surfaces.

It is also easily possible to use reflecting surfaces, for example mirrors, in the place of the prisms, which mirrors are arranged at the areas of the reflecting surfaces of the prisms.

I claim:

1. In a prism system for a stereoscopic microscope having a plurality of reflecting surfaces each deflecting one of a right and left beam path by 90°, the improvement comprising wherein four of said reflecting surfaces are provided in each beam path, wherein two of said surfaces in each beam path are reflection surfaces arranged in planes parallel with respect to an optic longitudinal axis of the microscope, and wherein the two other surfaces in each beam path are respectively inlet and outlet surfaces and are inclined at 45° with respect to the optic longitudinal axis and at 90° with respect to one another.

2. The prism system according to claim 1, wherein the two surfaces in each said beam path which are arranged in planes parallel with respect to the optic longitudinal axis define an angle of 90° with respect to one another.

3. The prism system according to claim 1, wherein the reflecting surfaces are each constructed as a hypotenuse surface of a rectangular prism member.

4. The prism system according to claim 3, wherein the prism member which includes the inlet surface in one of said beam paths rests on the prism member having the outlet surface of the other of said beam paths, with both surfaces adjoining one another.

5. The prism system according to claim 4, wherein the prism members which include the reflection surfaces are arranged each resting against one another or are arranged resting on the adjoining prism members which have the inlet surface or the outlet surface.

6. The prism system according to claim 3, wherein two of the prism members respectively having thereon the two reflection surfaces of a beam path are constructed in one piece.

7. The prism system according to claim 4, wherein each of the prism members which include the reflection surfaces in a beam path are constructed in one piece with the adjoining prism members, which respectively include the inlet and outlet surfaces.

8. The prism system according to claim 1, wherein the reflecting surfaces are constructed with a reflecting coating.

9. The prism system according to claim 1, wherein the reflecting surfaces each effect total reflection of a respective beam path.

10. A stereoscopic microscope for use in surgeries with a lens device and two ocular arrangements, wherein an area including parallel left and right beam paths includes a prism system having a plurality of reflecting surfaces each deflecting one of said right and said left beam path by 90°, wherein four of said reflecting surfaces are provided in each beam path, wherein two of said surfaces in each beam path are reflection surfaces arranged in planes parallel with respect to an optic longitudinal axis of the microscope, and wherein the two other surfaces in each beam path are respectively inlet and outlet surfaces and are inclined at 45° with respect to the optic longitudinal axis and at 90° with respect to one another.

11. The microscope according to claim 10, including near a lens device a collective lens and, arranged thereafter in a beam direction, a magnification changer, and wherein the prism system is constructed between the collective lens and the magnification changer.

12. The microscope according to claim 10, wherein the prism system is arranged between an ocular arrangement and a magnification changer of said microscope.

13. The microscope according to claim 10, wherein the prism system includes means for removing it from the beam path of the microscope while maintaining the normal function of the microscope.

* * * * *